United States Patent [19]

Petuch et al.

[11] Patent Number: 5,210,030
[45] Date of Patent: May 11, 1993

[54] PROCESS FOR SELECTIVELY ACYLATING IMMUNOMYCIN

[75] Inventors: Brian R. Petuch, Florence; Shieh-shung T. Chen, Morganville; Byron H. Arison, Watchung, all of N.J.

[73] Assignee: Merck & Co., Inc., Rahway, N.J.

[21] Appl. No.: 542,849

[22] Filed: Jun. 25, 1990

[51] Int. Cl.$^5$ .............. C12P 17/18; C12P 17/16; C12P 7/40; C12N 9/20
[52] U.S. Cl. .................... 435/119; 435/118; 435/136; 435/198
[58] Field of Search ............. 435/118, 119, 198, 136

[56] References Cited

U.S. PATENT DOCUMENTS 3,244,592  5/1966  Arai ................................. 435/119
4,894,366  1/1990  Okuhara et al. .................. 514/63

FOREIGN PATENT DOCUMENTS 0184162  6/1986  European Pat. Off. ........... 435/119
0323042  7/1989  European Pat. Off. ........... 435/119

OTHER PUBLICATIONS

Bianchi et al., *J. Org. Chem.*, vol. 53, pp. 5531–5534, 1988.
J. Antibiotics, A15, pp. 231–232, by Arai, et al.

Primary Examiner—Irene Marx
Attorney, Agent, or Firm—Salvatore C. Mitri; Charles M. Caruso

[57] ABSTRACT

Described is a new process for selectively acylating FK-506 type immunosuppressant macrolides, including immunomycin (FK-520), in the C-32 position, under novel conditions utilizing an immobilized lipase enzyme, an acyl donor, and a dry, non hydroxylic organic solvent. The enzyme is absorbed onto a solid support and the enzyme/support catalyzes the C-32 acylation. The enzyme/support complex can then be filtered from the reaction mixture and, recycled for use.

3 Claims, 1 Drawing Sheet

C-32 Acetyl FK-520

9388P/RJNge

PROCESS FOR SELECTIVELY ACYLATING IMMUNOMYCIN

BACKGROUND OF THE INVENTION

1. Field of the Invention

This invention relates to a new a process for producing C-32 acylated derivatives of FK-506 type immunosuppressant macrolides. The process involves contacting the FK-506 macrolide with an acyl donor, in the presence of an immobilized enzyme on a support under conditions which acylate the $C_{32}$ hydroxy group of the macrolide.

2. Brief Description of Disclosures in the Art

In 1983, the US FDA licensed cyclosporin, and extremely effective anti rejection drug that revolutionized the field of organ transplant surgery. The drug acts by inhibiting the body's immune system from mobilizing its vast arsenal of natural protecting agents to reject the transplant's foreign protein.

As effective as the drug is in fighting transplantation rejection, it suffers drawbacks in causing kidney failure, liver damage and ulcers which in many cases can be very severe.

EPO Publication No. 0184162 to Fujisawa, describes a new macrolide immunosuppressant FK-506 which is reputed to be 100 times more effective than cyclosporin. The macrolide is produced by fermentation of a particular strain of *Streptomyces tsukubaensis*. Also described are the closely related FK-506 type macrolide immunosuppressant FK-520, FK-523, FK-525 produced by fermentation. More specifically, Fujisawa discloses on page 3 a generic compound (I) having the structure:

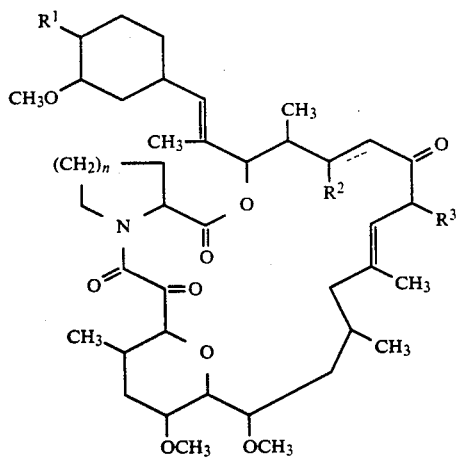

wherein
- $R^1$ is hydroxy or protected hydroxy,
- $R^2$ is hydrogen, hydroxy or protected hydroxy,
- $R^3$ is methyl, ethyl, propyl or allyl,
- n is an integer of 1 or 2, and
- the symbol of a line and dotted line is a single bond or a double bond, and salts thereof.

On page 32 of Fujisawa, there is disclosed a compound designated as FR-900506 having the structure:

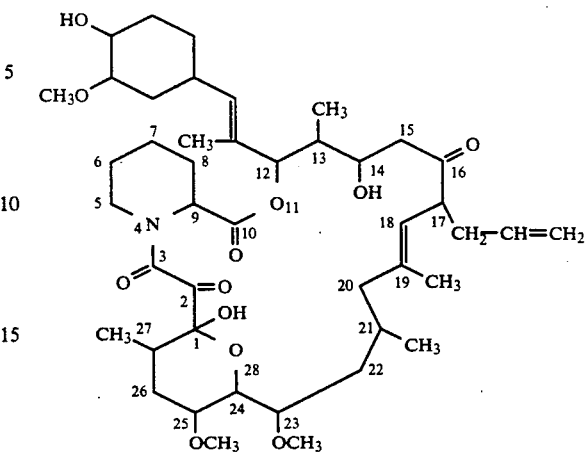

A compound designated as FR-900525 is shown by Fujisawa on page 36 as having the structure:

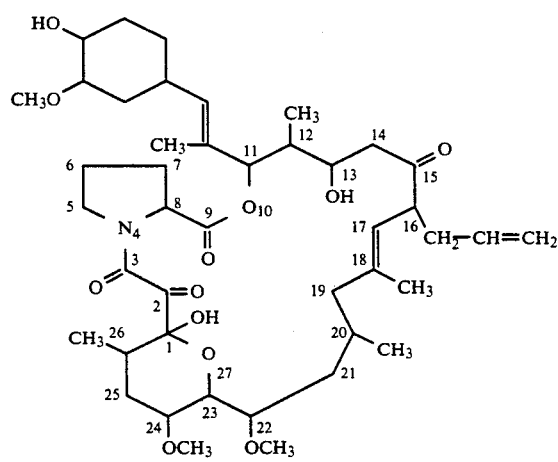

The compound designated as FR-900520 by Fujisawa on page 55 is shown as having the structure:

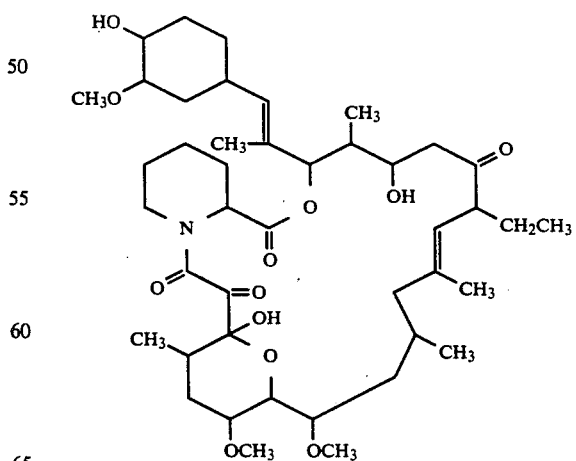

A compound designated as FR-900523 is shown by Fujisawa on page 59 as having the structure:

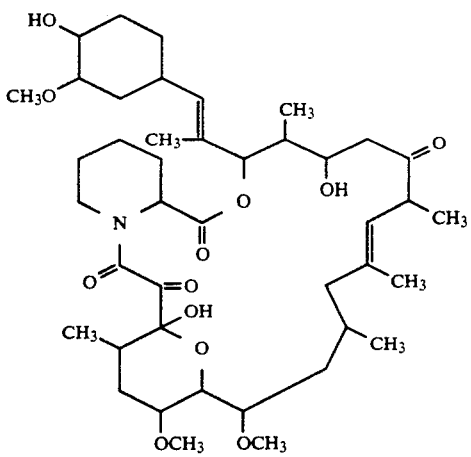

EPO Publication No. 0,323,042 to Fisons also described various derivatives of FK-506 type macrolides.

It is known in the art that acylation of hydroxy groups can be conducted with an acyl donor in the presence of pyridine solvent. However, after the reaction, the pyridine is difficult to remove and generally n-heptane is added to azeotropically remove the pyridine from the product.

It is also known in the art that immobilized lipase enzymes can be used as acylating agents to catalyze the stereoselective acylation of racemic alcohols. See D. Bianchi et al, *J. Org. Chem.*, 1988, vol 53, pp. 5531-5534. However, there is no suggestion that, where two or more available hydroxy groups are present in a large macrolide, i.e. FK-506, there may be a selectivity involved in the acylation.

What is desired is a simple, convenient method to selectively acylate the C-32 hydroxy function in FK-506 type macrolides without requiring the need for using pyridine, which is an environmental hazard.

SUMMARY OF THE INVENTION

Figure 1:
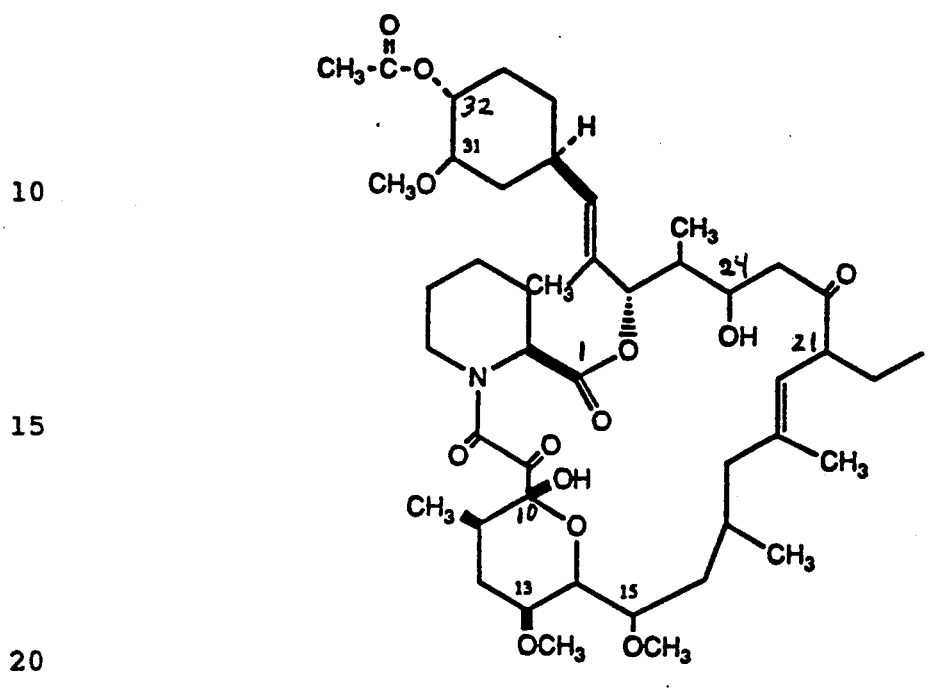
FIG. 1 is the assigned molecular structure of C-32 acetylated FK-520.

It has been found that FK-506 type macrolides can be selectively acylated in the C-32 position by contacting with an acyl donor in a dry inert organic solvent in the presence of a suspended, immobilized lipase enzyme on a support. After the reaction is complete, the suspended immobilized enzyme is filtered off and the C-32 acylated FK-506 type macrolide easily recovered.

In accordance with this invention, there is provided a process for selectively acylating the C-32 position in an FK-506 type macrolide comprising the step of contacting said FK-506 type macrolide with an acyl donor and a lipase enzyme immobilized on a support in a dry organic solvent, inert under the reaction conditions, excluding pyridine, for a sufficient time to obtain the C-32 acylated product.

DETAILED DESCRIPTION OF THE INVENTION AND PREFERRED EMBODIMENTS

The instant process involves the selective C-32 acylation of the C-32 hydroxy group on an FK-506 type macrolide.

By the term "FK-506 type macrolide" as used herein is meant the genus of compounds as described in EPO 0,184,182 and including FK-506, FK-520, FK-523 and FK 525.

The acyl donors useful in the process include carboxylic acid anhydrides and include acetic anhydride, propionic anhydride, butyric anhydride, and the like.

The lipase enzyme useful in the process is generically a lipolytic enzyme which can hydrolyze the ester groups in natural fats and oils. The enzymes are commercially available and preferably can be recovered from naturally occurring fungi, e.g. Aspergillus. When used in an aqueous environment, they catalyze de esterification. However, in a non-aqueous environment, they catalyze esterification. Representative examples of fungal lipase enzymes that successfully catalyze the C-32 acylation include lipase N(AMANO), L 1754 (SIGMA), LPL (AMANO), MA-10 (AMANO), AP-12 (AMANO).

The enzymes are immobilized on a support in which both the enzyme and support are insoluble in the solvent used in the process. The supports generically applicable in the process are those which are porous and can absorb the enzyme into holes and crevices not accessible to the solvent. The applicable supports are generically, diatomaceous earth, silica, polar organic polymers, and the like.

Representative examples include celite, pellicular silica, glass beads, polyacrylamide, and the like.

The immobilized enzyme/support is generally prepared by suspending the support in an aqueous solution of the enzyme in a phosphate buffer, allowing sufficient time for the support to absorb the enzyme completely onto the surface of the support and then drying the enzyme/support complex to obtain a free-flowing powder. Generally, about 2.5% of the enzyme/per weight of the support is utilized.

The solvents applicable in the process are dry organic solvents which are inert under the acylation conditions, i.e. nonhydroxylic liquids which are solvents for the FK-506 type macrolide and the acyl donor, but not for the enzyme. Specifically excluded is pyridine because of environmental considerations.

Representative classes of solvents include linear and branched ethers, aromatic hydrocarbons, chlorinated paraffins, lower carboxylic acid esters, and the like.

Examples are diethyl ether, tetrahydrofuran, 1,2-dimethoxyethane, benzene, toluene, mixed xylenes, ethylacetate, chloroform, methylene chloride, 1,2-dichloroethane, and the like.

The temperature of the reaction is usually conducted in the range of about 10° to 50° C., and preferably is carried out at room temperature.

Molar ratios of FK-506 macrolide: acyl donor are in the range of about 1:10.

Weight ratios of FK-506 macrolide: enzyme/support are in the range of about 1:30.

Generally the yields of C-32 acylated FK-506 type macrolide are in the range of 20 to 30% of theory.

The reaction workup is generally accomplished by filtering off the immobilized enzyme/support, which can be washed and recycled for further use, and isolating the C-32 acylated product from the remaining mother liquor by conventional means such as HPLC liquid chromatography, distillation or crystallization. Conventional apparatus can be utilized for carrying out the process.

A continuous process can also be carried out by the use of the immobilized enzyme/support in columns, where solutions of the FK-506 macrolides are slowly percolated through the columns to allow C-32 acylation to occur and then continuously isolated and purified.

The following examples are given for the purpose of illustrating the present invention and should not be construed as being limitations on the scope or spirit of the instant invention.

EXAMPLE 1

Enzymatic Acetylation of FK-520

A. Immobilization of Enzyme

Enzymes were immobilized according to the Procedure of Bianchi, et al, 1988, J. Org. Chem., 53, 5531–5534. Celite 535 (2 g) (Source) was washed once with distilled water, followed by a single wash with 100 mM pH 7.0 phosphate buffer. The Celite was mixed with a lipase N enzyme solution (0.5 g enzyme in 10 ml 100 mM pH 7 phosphate buffer) and placed in a fume hood to dry overnight. After drying, the moisture content was further reduced by drying in a rotary evaporator at 40° C., under reduced pressure. Drying ceased when the enzyme/support complex became a free-flowing powder.

B. Enzymatic Reacton Conditions

300 Mg of immobilized enzyme/support was added to 10 ml anhydrous benzene containing 50 μl acetic anhydride and 10 mg FK-520. The reaction mixture was incubated overnight at room temperature with moderate shaking. After incubation, the solid enzyme/support was removed by filtration.

C. Purification

The reaction mixture was evaporated to dryness, dissolved in 45% aqueous acetonitrile and subjected to purification using the following conditions:

| | |
|---|---|
| Column: | Whatman $C_{18}ODS$-3 |
| | 5 micron, 9.4 mm × 25 mm |
| Temp: | 57° C. |
| Flow Rate: | 3.75 ml/min. |
| Mobile Phase: | 45% to 80% aqueous acetonitrile +0.1% $H_3PO_4$ gradient over 30 minutes. |
| Detection: | 210 and 225 nm UV. |

Following preparative chromatography, 2,8 mg of material was isolated and submitted for NMR analysis.

D. Identification

Following NMR analysis which confirmed the assigned structure on the figure, the solid was identified as 32-acetyl FK-520.

What is claimed is:

1. A process for selectively acylating the C-32 position in a macrolide which comprises:
    (a) contacting a macrolide which is a member selected from the group consisting of FK-506, FK-520, FK-523 and FK-525,
    (b) with an acyl donor which is a member selected from the group consisting of acetic anhydride, propionic anhydride, butyric anhydride, trifluoroacetic anhydride and mixtures thereof,
    (c) in the presence of fungal AMANO lipase N enzyme immobilized on a solid support,
    (d) in an inert, dry organic solvent which is a member selected from the group consisting of aromatic hydrocarbons, linear ethers, branched ethers, halogenated paraffins, and lower carboxylic acid esters,
    (e) at a temperature range of 10° to 50° C.,
    (f) for a period of time sufficient to obtain said C-32 acylated product; and,
    (g) recovering said C-32 acylated product.

2. The process of claim 1, wherein the molar ratios of macrolide: acyl donor is 1:10.

3. The process of claim 1 wherein said support is diatomaceous earth, silica, glass beads or a polar organic polymer.

* * * * *